US008591545B2

(12) United States Patent
Lunn et al.

(10) Patent No.: US 8,591,545 B2
(45) Date of Patent: Nov. 26, 2013

(54) FLAT SUTURE ANCHOR

(75) Inventors: Richard M. Lunn, Kingston, MA (US);
David A. Paulk, Hopedale, MA (US);
Paul L. Salvas, Norton, MA (US)

(73) Assignee: Smith & Nephew, Inc., Andover, MA (US)

( * ) Notice: Subject to any disclaimer, the term of this patent is extended or adjusted under 35 U.S.C. 154(b) by 173 days.

(21) Appl. No.: 13/072,384

(22) Filed: Mar. 25, 2011

(65) Prior Publication Data
US 2012/0245631 A1 Sep. 27, 2012

(51) Int. Cl.
A61B 17/04 (2006.01)
A61B 17/84 (2006.01)
F16B 15/00 (2006.01)

(52) U.S. Cl.
USPC ............................ 606/232; 606/75; 411/457

(58) Field of Classification Search
USPC ................. 606/104, 75, 219, 220, 232, 300; 411/457, 461–465, 467, 468
See application file for complete search history.

(56) References Cited

U.S. PATENT DOCUMENTS

| 5,181,919 A | 1/1993 | Bergman et al. |
| 5,217,486 A * | 6/1993 | Rice et al. .................. 606/232 |
| 5,520,700 A * | 5/1996 | Beyar et al. .................. 606/232 |
| 5,720,753 A * | 2/1998 | Sander et al. ................. 606/104 |
| 5,984,927 A * | 11/1999 | Wenstrom et al. ............. 606/75 |
| 6,200,330 B1 * | 3/2001 | Benderev et al. ............. 606/232 |
| 8,394,097 B2 * | 3/2013 | Peyrot et al. .................. 606/75 |
| 2003/0023268 A1 | 1/2003 | Lizardi |
| 2005/0075668 A1 | 4/2005 | Lizardi |
| 2006/0229671 A1 | 10/2006 | Steiner et al. |
| 2006/0253119 A1 | 11/2006 | Berberich et al. |
| 2008/0004659 A1 | 1/2008 | Burkhart et al. |
| 2008/0109037 A1 | 5/2008 | Steiner et al. |
| 2008/0275431 A1 | 11/2008 | Stone et al. |
| 2009/0018554 A1 | 1/2009 | Thorne et al. |
| 2009/0112270 A1 | 4/2009 | Lunn et al. |
| 2010/0016869 A1 | 1/2010 | Paulk et al. |

FOREIGN PATENT DOCUMENTS

EP 0835640 A1 4/1998

* cited by examiner

*Primary Examiner* — Julian W Woo
(74) *Attorney, Agent, or Firm* — Pierce Atwood LLP; Joseph M. Maraia

(57) ABSTRACT

A suture anchor for anchoring a suture to a bone, including a distal end having a bifurcated tip, in which the bifurcated tip defines a suture-engaging slot, a proximal end, a longitudinal axis between the distal end and the proximal end, and two substantially flat surfaces extending between the distal end and the proximal end, in which the two substantially flat surfaces are substantially parallel, in which the two substantially flat surfaces are separated by a thickness of no more than about 0.1 inches, and in which the two substantially flat surfaces extend along an axis perpendicular to the longitudinal axis by a width of no more than about 0.4 inches.

11 Claims, 9 Drawing Sheets

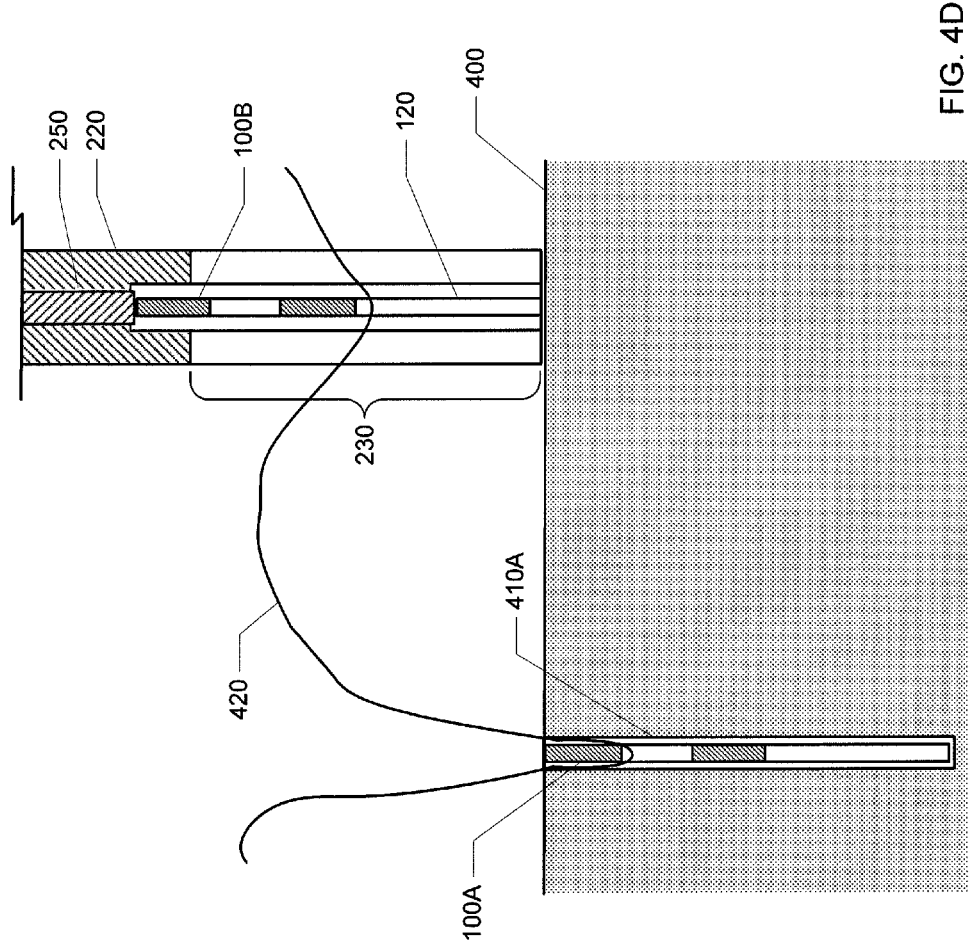

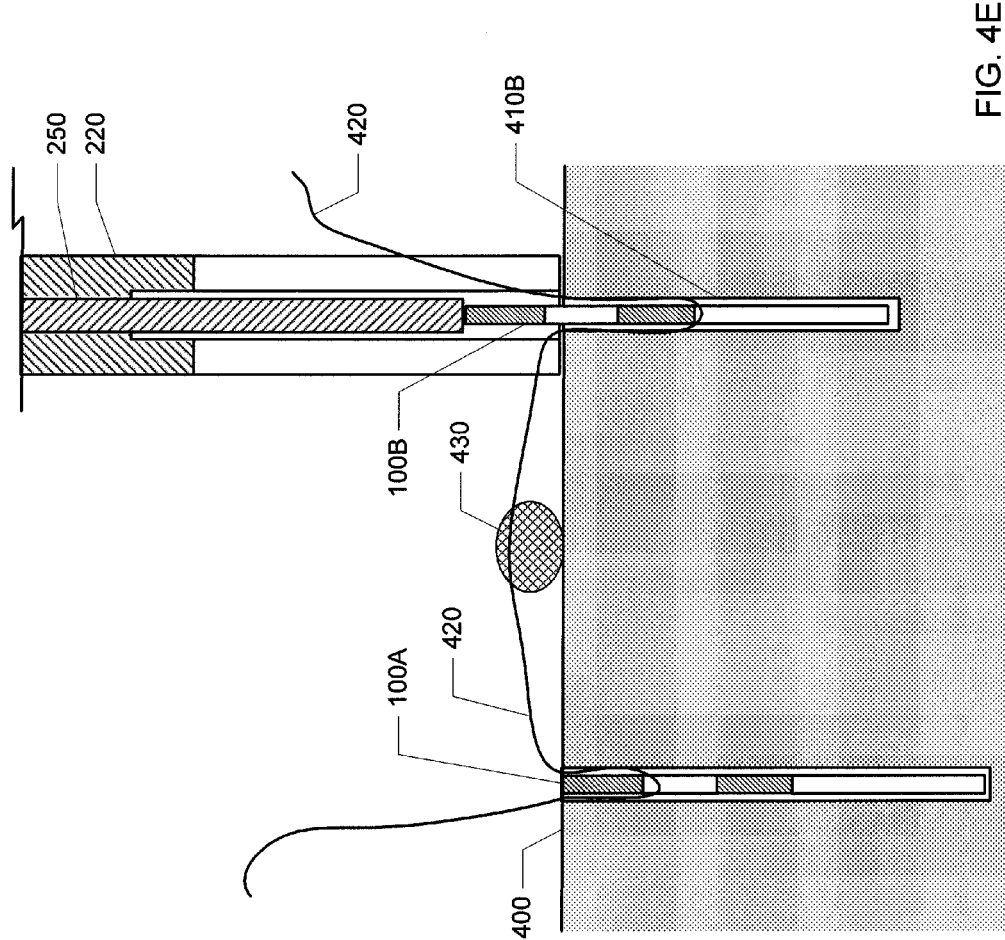

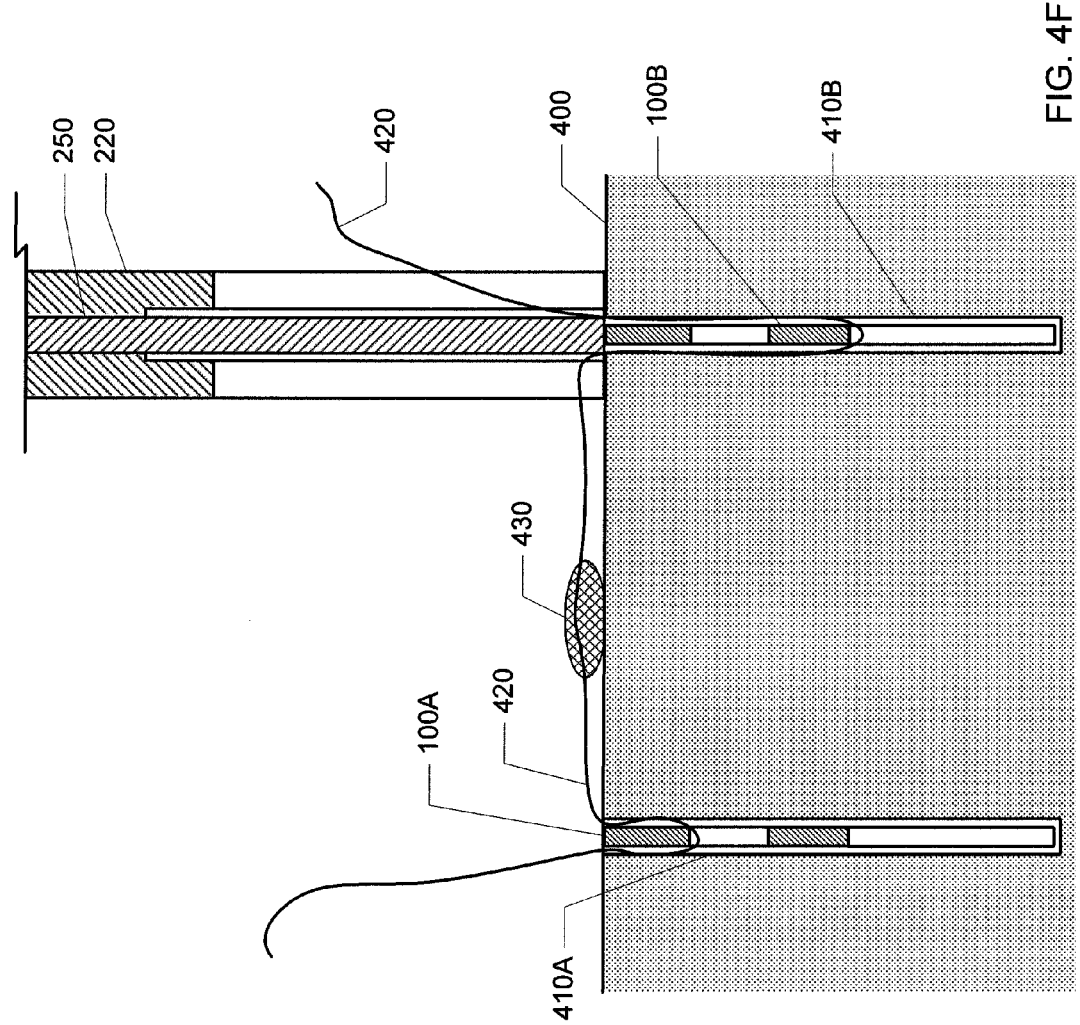

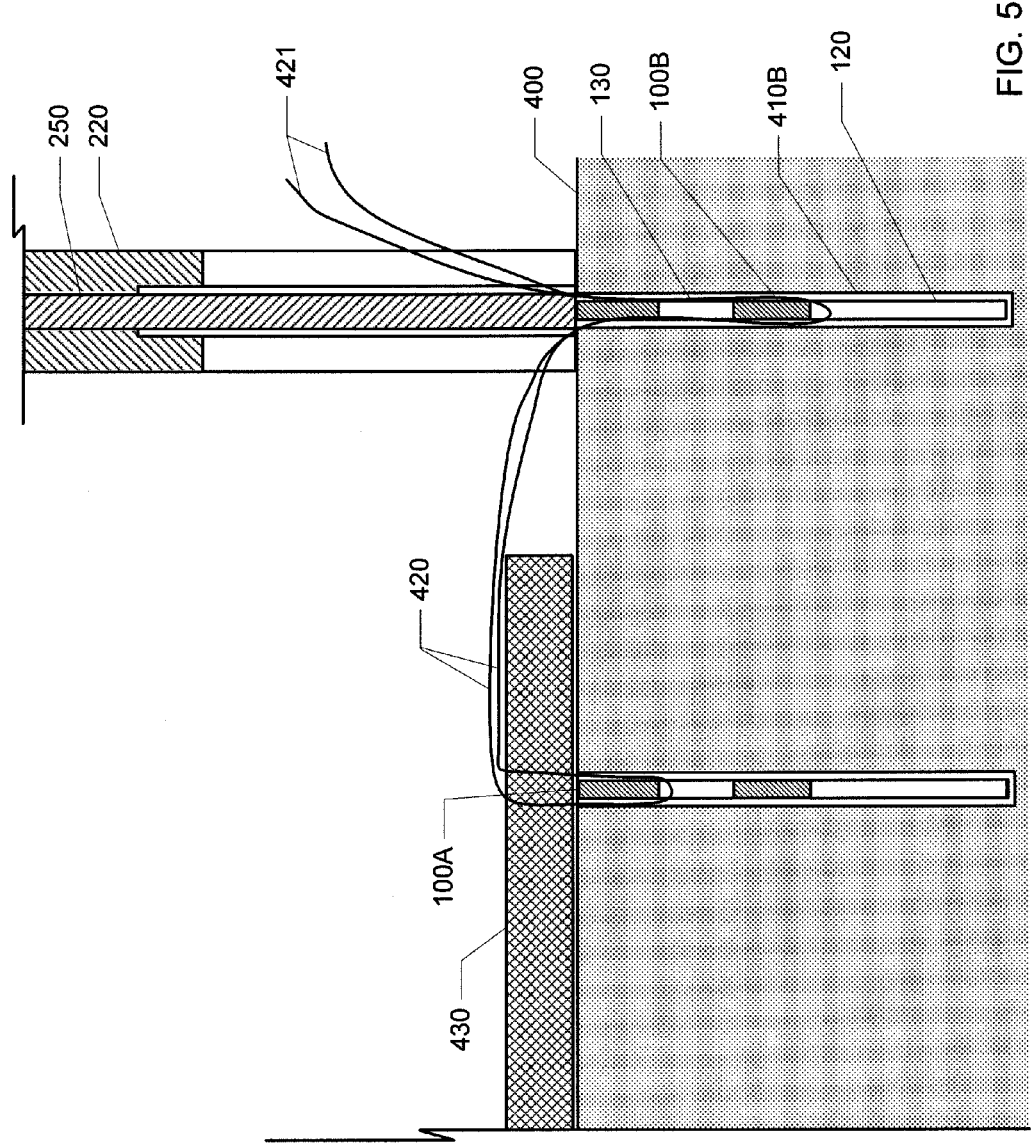

FLAT SUTURE ANCHOR

BACKGROUND OF INVENTION

1. Field of the Invention

Embodiments disclosed herein relate generally to surgical devices. Specifically, embodiments disclosed herein relate to an anchor for anchoring a suture within a patient's body.

2. Background

In the human body, soft tissues such as tendons, ligaments, and muscles are generally attached to bones of the skeleton. In some injuries or conditions, such soft tissues may become fully or partially detached from the corresponding bones. For example, common sports injuries may include damage to tendons or ligaments in the shoulder, hip, ankle, knee, elbow, and/or foot.

To treat such injuries, it may be necessary to attach a soft tissue to a bone. For example, in the event that a tendon has been torn away from a bone, the proper treatment may include surgery to reattach the tendon to the bone.

One technique for attaching a soft tissue to a bone is to use a suture anchor to attach a suture to the bone, and tying the suture to the soft tissue. Conventionally, such suture anchors are inserted into boreholes drilled into the bone. As a result, before such an anchor can be inserted, a surgeon must first determine a borehole location, drill the borehole, and attach the suture to the anchor. Further, in the case of some conventional suture anchors, attaching the suture to the suture anchor may require tying the suture to the suture anchor. Such preparation can be tedious and time consuming, and can prolong the time required to perform a surgical operation.

Accordingly, there exists a need for a suture anchor that may be rapidly prepared and inserted in a bone without requiring extensive preparation of the bone.

SUMMARY OF INVENTION

It is an object of the present invention to provide a suture anchor for anchoring a suture within a patient's body.

According to one aspect of the present invention, there is provided a suture anchor for anchoring a suture to a bone, comprising a distal end having a bifurcated tip, in which the bifurcated tip defines a suture-engaging slot, a proximal end, a longitudinal axis between the distal end and the proximal end, and two substantially flat surfaces extending between the distal end and the proximal end, in which the two substantially flat surfaces are substantially parallel, in which the two substantially flat surfaces are separated by a thickness of no more than about 0.1 inches, and in which the two substantially flat surfaces extend along an axis perpendicular to the longitudinal axis by a width of no more than about 0.4 inches.

According to one aspect of the present invention, there is provided an insertion tool, comprising a proximal end and a distal end, a longitudinal axis between the distal end and the proximal end, a handle disposed on the proximal end, an outer tube extending from the handle along the longitudinal axis and comprising an inner bore, a driver rod movably disposed within the inner bore, and a recessed cavity disposed on the distal end of the outer tube and aligned with the longitudinal axis, in which the recessed cavity is configured to retain a suture anchor, comprising two substantially flat parallel surfaces, for insertion into a bone.

According to one aspect of the present invention, there is provided a system, comprising an insertion tool and a suture anchor. The insertion tool comprises a proximal end and a distal end, a longitudinal axis between the distal end and the proximal end, a handle disposed on the proximal end, an outer tube extending from the handle along the longitudinal axis and comprising an inner bore, a driver rod moveably disposed within the inner bore, and a recessed cavity disposed on the distal end of the outer tube and aligned with the longitudinal axis. The suture anchor is engaged in the recessed cavity in a first position, and comprises a bifurcated tip defining a suture-engaging slot, two substantially flat parallel surfaces, in which the two substantially flat surfaces are separated by a thickness of no more than about 0.1 inches, and in which the two substantially flat surfaces extend along an axis perpendicular to the longitudinal axis by a width of no more than about 0.4 inches.

According to one aspect of the present invention, there is provided a method of inserting a suture anchor, comprising providing a suture anchor having two substantially flat surfaces and a bifurcated tip, mechanically engaging a suture with the suture anchor, and inserting the suture anchor into a bone, in which the bifurcated tip comprises two sharpened points for insertion into the bone.

According to one aspect of the present invention, there is provided a method of anchoring a suture, comprising passing a first portion of the suture through a transverse opening of a first suture anchor, in which the transverse opening is between two substantially flat parallel surfaces of the first suture anchor, inserting the first suture anchor into a bone at a first location to fix the first portion of the suture at the first location, passing a second portion of the suture in a bifurcated tip of a second suture anchor, in which the first and second suture anchors are substantially identical, and inserting the second suture anchor into the bone at a second location to fix the second portion of the suture at the second location.

BRIEF DESCRIPTION OF DRAWINGS

FIGS. 4A-4F are multiple views of an example according to embodiments disclosed herein.

FIG. 5 is a view of an example according to embodiments disclosed herein.

DETAILED DESCRIPTION

In one aspect, embodiments disclosed herein relate to an anchor for anchoring a suture within a patient's body. Specifically, embodiments disclosed herein relate to an anchor for anchoring a suture to a bone within a patient's body.

Embodiments of a suture anchor having a substantially flat body disclosed herein may provide a means for anchoring a suture to a bone within a human body. The suture anchor, according to embodiments disclosed herein, may allow for insertion into a bone without requiring prior preparation of the bone. The suture anchor, according to embodiments disclosed herein, may also allow a surgeon to attach a suture to the suture anchor by threading the suture through a transverse opening, and/or by capturing the suture in a slot defined by a bifurcated tip of the suture anchor. Further, embodiments of an installation tool disclosed herein may provide a means for insertion of the suture anchor in a bone. The installation tool, according to embodiments disclosed herein, may allow one or more sutures to be engaged to the suture anchor prior to insertion in the bone.

Figure 1A:
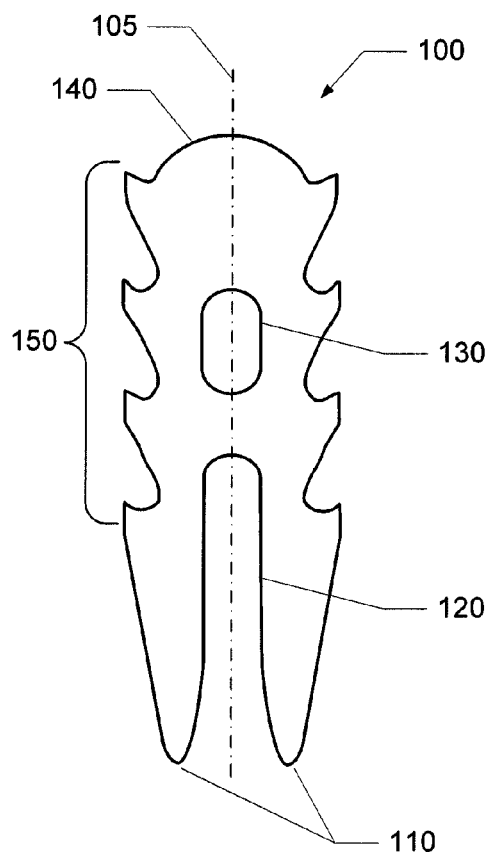
FIGS. 1A-1C are drawings of multiple views of a suture anchor in accordance with embodiments disclosed herein.
Figure 1B:
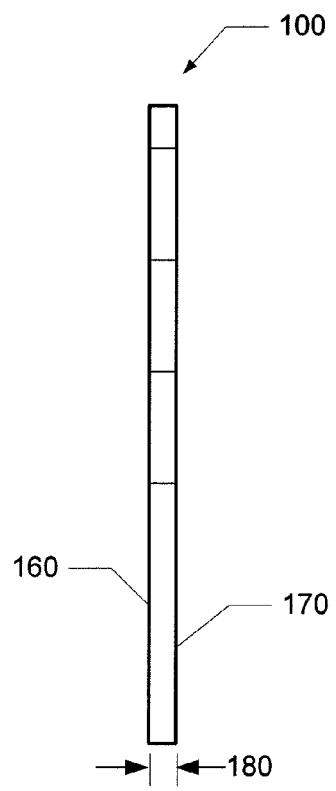
Figure 1C:
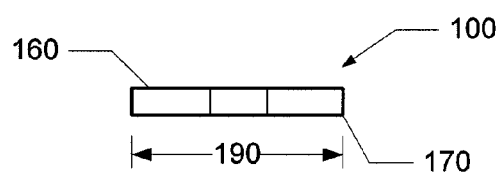

Referring, generally, to FIGS. 1A-1C, a suture anchor 100 in accordance with embodiments disclosed herein is shown. FIG. 1A shows a front view of the suture anchor 100. The suture anchor 100 is an apparatus for anchoring a suture within a body. Specifically, the suture anchor 100 is an apparatus for anchoring tissue (not shown) to a bone (not shown). As shown, the suture anchor 100 includes a bifurcated tip 110 defining a suture-engaging slot 120, one or more retention barbs 150, a transverse opening 130, a driving surface 140, and a longitudinal axis 105. As described below, in one or more embodiments, the suture anchor 100 may be configured to be driven along the longitudinal axis 105 for insertion into a bone (not shown). In one or more embodiments, the suture anchor 100 may be mounted in an installation tool (described below with reference to FIGS. 2A, 2B, and 3) for insertion into a bone.

FIG. 1B shows a side view of the suture anchor 100. As shown, in one or more embodiments, the suture anchor 100 may have a substantially flat body. Specifically, the suture anchor 100 may have two substantially flat surfaces, namely a first surface 160 and a second surface 170. In one or more embodiments, the first surface 160 and the second surface 170 may be substantially parallel, and may be separated by a thickness 180. In one or more embodiments, the thickness 180 may be no more than about 0.1 inches. As shown, the retention barbs 150 may be disposed along two exterior lateral edges of the first surface 160 and the second surface 170 (defined by the thickness 180). In one or more embodiments, the retention barbs 150 may be configured to retain the suture anchor 100 within a bone into which the suture anchor 100 is inserted.

FIG. 1C shows a bottom view of the suture anchor 100. As shown, the first surface 160 and the second surface 170 may each extend laterally (i.e., perpendicularly to the longitudinal axis 105) for a width 190. In one or more embodiments, the width 190 may be no more than about 0.4 inches.

As shown, in one or more embodiments, the width 190 may be substantially larger than the thickness 180, thereby providing the suture anchor with a substantially thin line of insertion into the bone. In one or more embodiments, the ratio of the thickness 180 to the width 190 may be selected from a range of values. In or more embodiments, this ratio may be selected so as to reduce the mechanical force required to drive the suture anchor 100 into the bone, and to reduce the damage to the bone. For example, the ratio of the thickness 180 to the width 190 may be selected from within a range of 1:2 to 1:4. In another example, the ratio of the thickness 180 to the width 190 may be selected from within a range of 1:4 to 1:8.

In one or more embodiments, the bifurcated tip 110 may include two sharpened points configured to enable insertion into a bone. For example, the bifurcated tip 110 may be configured to ease insertion of the suture anchor 100 into a bone without requiring any prior preparation such as pre-drilling a borehole into the bone. In one or more embodiments, the body of the suture anchor 100 is substantially rigid. For example, the suture anchor 100 may be configured to be driven into the bone without substantial deformation and/or breakage.

Once inserted into the bone, the friction between the large surface area of the suture anchor 100 (i.e., first surface 160 and second surface 170) and the bone interface causes the suture anchor 100 to be retained firmly within the bone. Further, the retention barbs 150 along the sides of the suture anchor 100 substantially increase the difficulty of the suture anchor 100 being removed from the bone. Thus, in one or more embodiments, a suture anchor 100, having been inserted into a bone, may be retained within the bone by surface friction and/or the retention barbs 150.

As described above, the bifurcated tip 110 defines the suture-engaging slot 120. In one or more embodiments, the suture-engaging slot 120 may be configured to capture a suture (not shown) passing between the two points of the bifurcated tip 110. Further, the suture-engaging slot 120 may be configured to fixedly engage the suture when the suture anchor 100 is inserted into a bone. For example, assume that a suture anchor 100 having a suture engaged in the suture-engaging slot 120 is inserted into a bone. In this example, the suture will be anchored to the bone both by the suture being engaged in the suture-engaging slot 120 and by the suture being wedged between the external surface area of the suture anchor 100 (i.e., first surface 160 and second surface 170) and the bone. In another example, assume that a surgeon has tied a knot in the suture, and that the knot is large enough to not be able to pass through the suture-engaging slot 120. Further, assume that the surgeon has tied the knot on the opposite side of the suture anchor 100 from the side where any tension may be applied to the suture. In this example, the suture will also be anchored to the bone due to the knot being unable to pass through the suture-engaging slot 120.

In one or more embodiments, the transverse opening 130 may be configured to enable one or more sutures to pass through the suture anchor 100 (i.e., to traverse from the first surface 160 to the second surface 170), and to enable such sutures to be fixedly engaged to the suture anchor 100. For example, a surgeon may pass a suture through the transverse opening 130 and tie a knot in the suture, thereby engaging the suture to the suture anchor 100. The surgeon may then insert the suture anchor 100 into a bone, thereby anchoring the suture to the bone both by the suture being engaged in the transverse opening 130 and by the suture being wedged between the external surface area of the suture anchor 100 (i.e., first surface 160 and second surface 170) and the bone. Further, as described below with reference to FIGS. 4F and 5, the suture may be engaged to a soft tissue (e.g., ligament, tendon, muscle, etc.), thereby securing the soft tissue to the bone.

In one or more embodiments, the suture anchor 100 can be made from any material or combination of materials, without limitation (e.g., a metal, a plastic, a ceramic, a combination of metal and plastic, etc.). Further, in one or more embodiments, the suture anchor 100 may be made of biodegradable materials. For example, the suture anchor 100 may be made of metals such as, but not limited to, stainless steel, titanium, or any bio-compatible metal. In another example, the suture anchor 100 may be made of plastics such as, but not limited to, PEEK, polyethylene, PLLA, or any non-metallic material capable of withstanding the force required to drive the suture anchor 100 into a bone.

Figure 2A:
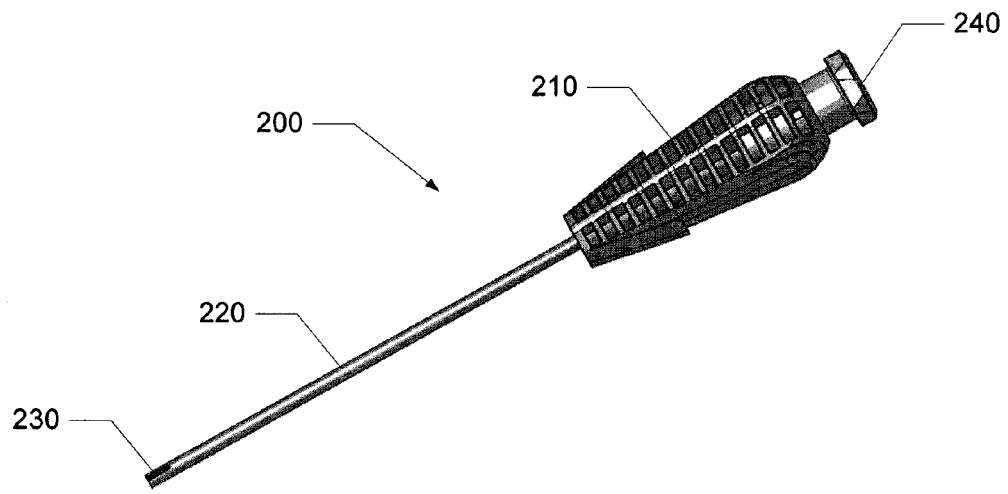
FIGS. 2A-2B are drawings of an installation tool in accordance with embodiments disclosed herein.
Figure 2B:
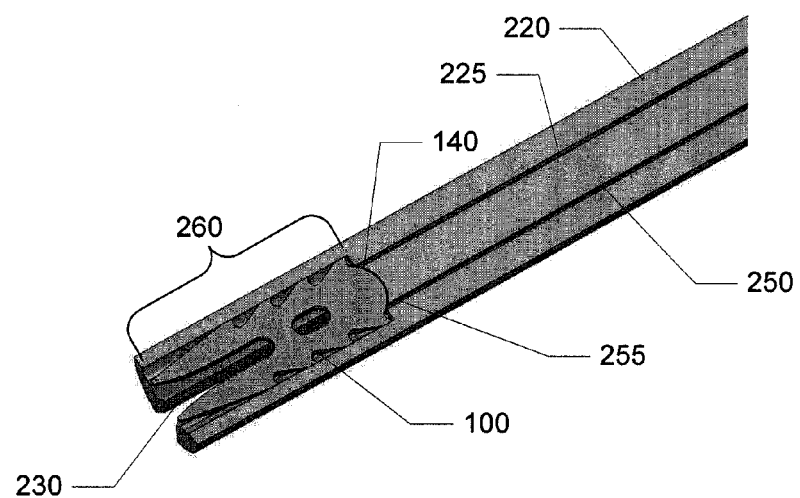
Figure 3:
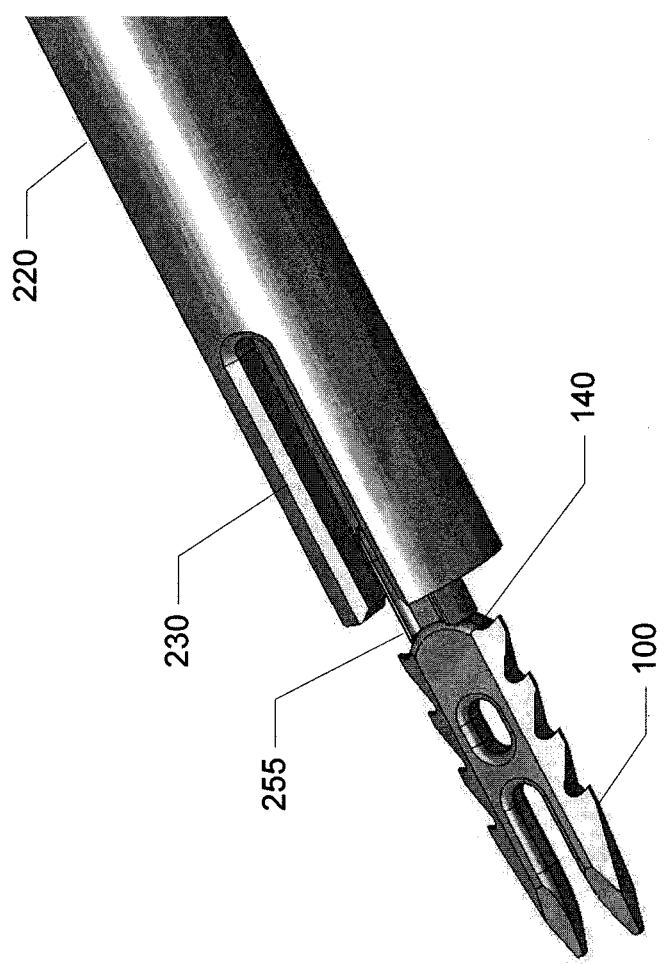
FIG. 3 is a close-up view of an installation tool and a suture anchor according to embodiments disclosed herein.

Referring now to FIGS. 2A-2B and 3, an installation tool 200 in accordance with embodiments disclosed herein is shown. The installation tool 200 is an apparatus for inserting the suture anchor 100 (shown in FIGS. 1A-1C) in a bone. As shown in FIG. 2A, the installation tool 200 may include a handle 210, an outer tube 220, a transverse slot 230 disposed on a distal end of the outer tube 220, and an impact surface 240 disposed on the proximal end of the handle 210.

Referring now to FIGS. 2B and 3, a cut-away view and a detail view of the distal end of the outer tube 220 are shown, respectively. As shown, the installation tool 200 may also include a driver rod 250 and a recessed cavity 260, both disposed within the outer tube 220. In one or more embodiments, the driver rod 250 may be mechanically engaged with the impact surface 240. Further, the driver rod 250 may be configured to move longitudinally within the outer tube 220 when a mechanical force is applied to the impact surface 240. In one or more embodiments, the driver rod 250 may include a distal end 255 configured to engage the driving surface 140 of a suture anchor 100 disposed within the recessed cavity 260. For example, in one or more embodiments, the distal end 255 may have a concave curvature matching a convex curvature of the driving surface 140.

In one or more embodiments, the recessed cavity 260 may be open on the distal end of the outer tube 220, and may be configured to retain a suture anchor 100 until the suture anchor 100 is inserted into a bone by the driver rod 250. For example, FIG. 3 shows the suture anchor 100 being ejected out of the recessed cavity 260 by the driver rod 250 as is the case when the suture anchor 100 is fully inserted into the bone.

In one or more embodiments, the recessed cavity 260 may be configured to be optionally reloaded with new suture anchors 100. For example, after a first suture anchor 100 is inserted into a bone, the driver rod 250 may be withdrawn back into the outer tube 220 to allow room for a second suture anchor 100 to be inserted into the recessed cavity 260 though the opening at the distal end of the outer tube 220. In this manner, the installation tool 200 may be used to insert suture anchors 100 then be reloaded any required number of times.

In one or more embodiments, the transverse slot 230 is configured to enable one or more sutures to be engaged to a suture anchor 100 when it is located within the recessed cavity 260. For example, a surgeon may use the transverse slot 230 to pass a suture through the transverse opening 130 and/or the suture-engaging slot 120 of the suture anchor 100 located within the recessed cavity 260. As shown, in one or more embodiments, the transverse slot 230 is open to the distal end of the outer tube 220, thus enabling the suture, when engaged to a suture anchor 100 being inserted into a bone, to exit the transverse slot 230 along with the suture anchor 100.

In one or more embodiments, the suture anchor 100 may be inserted into a bone by providing an impact force on the impact surface 240. For example, a surgeon may install the suture anchor 100 by positioning the installation tool 200 at a desired insertion location on the bone, and then striking the impact surface 240 with a hammer (or any means of applying the necessary force). Because the impact surface 240 is connected to the driver rod 250, the mechanical force resulting from the hammer strike is transferred to the suture anchor 100 via the driver rod 250, thereby causing the suture anchor 100 to be driven out of the recessed cavity 260 and into the bone.

Figure 4C:
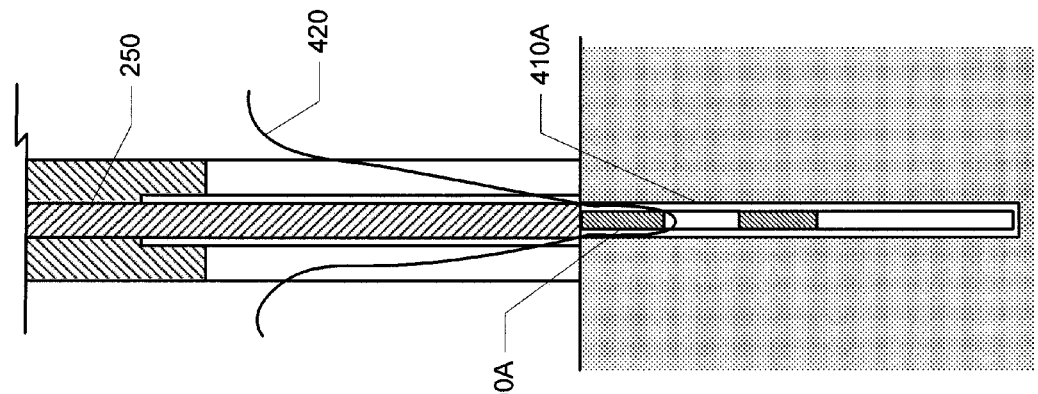
Figure 4B:
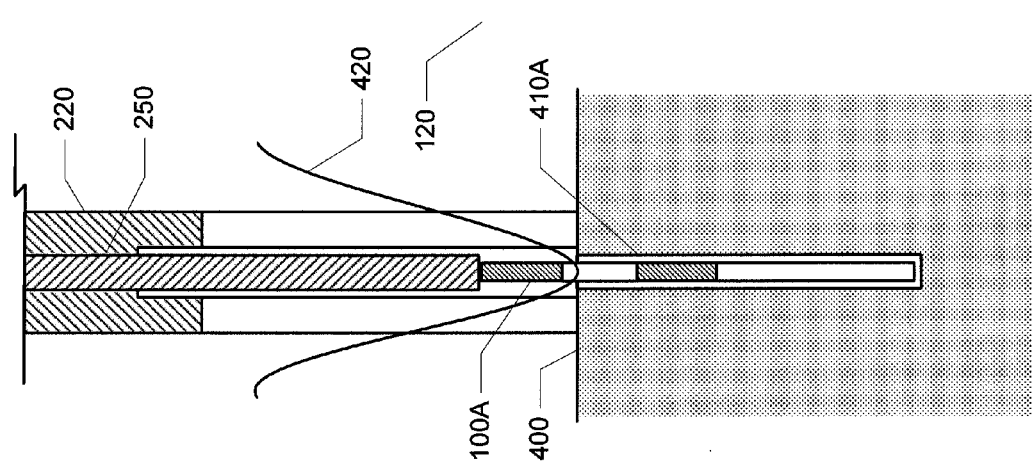
Figure 4A:
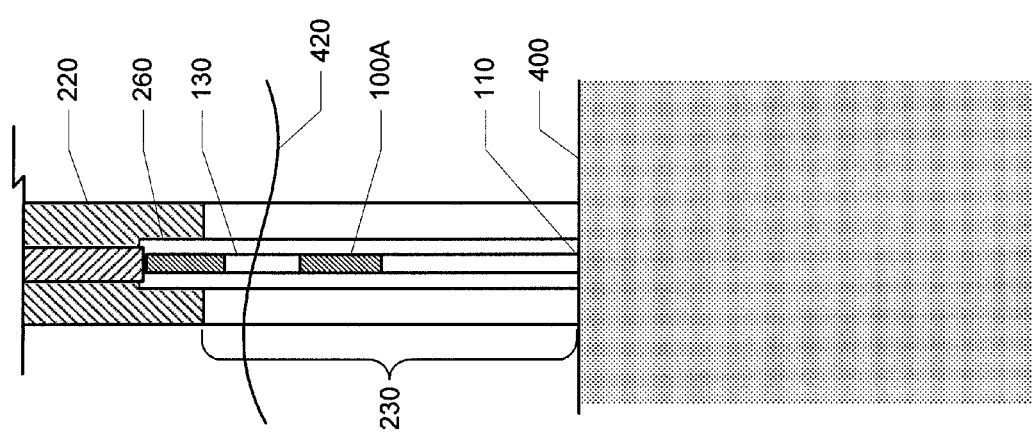

Referring now to FIGS. 4A-4F, an example of using suture anchors 100 to secure a suture at two locations of a bone is shown at multiple points in time, in accordance to embodiments disclosed herein. FIG. 4A shows a section view of the distal end of an outer tube 220 in contact with a bone 400 at a first point in time. As shown, a first suture anchor 100A is loaded within the recessed cavity 260, such that the bifurcated tip 110 is also in contact with a surface of the bone 400. Further, a suture 420 has been passed through the transverse slot 230 of the outer tube 220, and through the transverse opening 130 of the first suture anchor 100A.

Referring now to FIG. 4B, a second point in time of the example is shown, in accordance to embodiments disclosed herein. As shown, at the second point in time, the driver rod 250 has been moved partially downward within the outer tube 220. For example, assume that a surgeon has applied an impact force to the impact surface 240 of the installation tool 200 (shown in FIG. 2A), thereby causing the driver rod 250 to move downward within the outer tube 220. Accordingly, as shown in FIG. 4B, the first suture anchor 100A is partially driven into the bone 400, thereby creating a first insertion location 410A within the bone 400. Note that, because the suture 420 is engaged through the transverse opening 130 of the first suture anchor 100A, the suture 420 is moved downward along with the first suture anchor 100A.

Referring now to FIG. 4C, a third point in time of the example is shown, in accordance to embodiments disclosed herein. As shown, at the third point in time, the driver rod 250 has been moved fully downward within the outer tube 220. Accordingly, as shown, the first suture anchor 100A has been driven fully into the first insertion location 410A. Further, the suture 420 has also been driven into the first insertion location 410A. Accordingly, in this position, the suture 420 is held in place both by its attachment to the first suture anchor 100A at the transverse opening 130 and by being pinched between the first suture anchor 100A and the first insertion location 410A, thereby securing the suture 420 to the first insertion location 410A.

Referring now to FIG. 4D, a fourth point in time of the example is shown, in accordance to embodiments disclosed herein. As shown, at the fourth point in time, a second suture anchor 100B has been loaded into the recessed cavity 260, and the distal end of the outer tube 220 has been positioned at a different location of the bone 400. Further, the transverse slot 230 has been positioned over the suture 420, such that the suture 420 is captured within the suture-engaging slot 120 of the second suture anchor 100B.

Referring now to FIG. 4E, a fifth point in time of the example is shown, in accordance to embodiments disclosed herein. As shown, at the fifth point in time, a tissue 430 has been engaged between the suture 420 and the surface of the bone 400. Assume that the tissue 430 is a soft tissue (e.g., ligament, tendon, muscle, etc.) which is desired to be attached to the bone 400. Further, the driver rod 250 has been moved partially downward within the outer tube 220, thereby causing the second suture anchor 100B to be partially driven into the bone 400. Accordingly, the bifurcated tip 110 of the second suture anchor 100B has broken the surface of the bone 400, thereby creating a second insertion location 410B within the bone 400. Further, because the suture 420 is engaged through the suture-engaging slot 120 of the second suture anchor 100B, the suture 420 is moved downward along with the second suture anchor 100B. Note that, in the example shown in FIG. 4E, the longitudinal axis of the tissue 430 is perpendicular to the length of the suture 420 extending between the first suture anchor 100A and the second suture anchor 100B.

Referring now to FIG. 4F, a sixth point in time of the example is shown, in accordance to embodiments disclosed herein. As shown, at the sixth point in time, the driver rod 250 has been moved fully downward within the outer tube 220. Accordingly, as shown, the second suture anchor 100B has been driven fully into the second insertion location 410B. Further, the suture 420 has also been driven into the second insertion location 410B, thereby shortening the portion of the suture 420 extending between the first insertion location 410A and the second insertion location 410B. Accordingly, in this position, the suture 420 is held in place both by its attachment to the second suture anchor 100B at the suture-engaging slot 120 and by being pinched between the second suture anchor 100B and the second insertion location 410B, thereby securing the suture 420 to the second insertion location 410B. Furthermore, the suture 420 has been pulled tightly between the first insertion location 410A and the second insertion location 410B, thereby causing the tissue 430 to be held firmly against the bone 400.

Referring now to FIG. 5, an example of an alternative technique of engaging the suture 420 is shown. In this example, a surgeon has passed two portions of the suture 420 through a tissue 430 placed adjacent to the bone 400. Further, the surgeon has captured the two portions of the suture 420 through the suture-engaging slot 120 of the second suture anchor 100B, and has driven the second suture anchor 100B into the bone 400. Optionally, the surgeon may then optionally tie the two suture ends 421 into a knot (not shown) to secure the suture 420 to the second suture anchor 100B. Alternatively, the suture 420 may be secured only by being pinched between the second suture anchor 100B and the second insertion location 410B. In this manner, the tissue 430 may be anchored to the bone 400. Note that, in the example shown in FIG. 5, the longitudinal axis of the tissue 430 is parallel to the two portions of the suture 420 extending between the first suture anchor 100A and the second suture anchor 100B. Other alternatives, such as capturing only one of the two portions of the suture 420 through the suture-engaging slot 120 and capturing one or both portions of the suture 420 through the transverse opening 130, rather than through the suture-engaging slot 120, are also within the scope of this technique.

In a further alternative, it would also be possible to use only one of the anchors 100 to fixate tissue to bone. For example, as in FIG. 5, once the tissue 430 has been placed adjacent to bone 400, the two portions of the suture 420 may be passed through the tissue 430 and the suture portions 420 may then be tied to form a knot, thereby fixating the tissue 430 to the bone 400.

Figure 6:
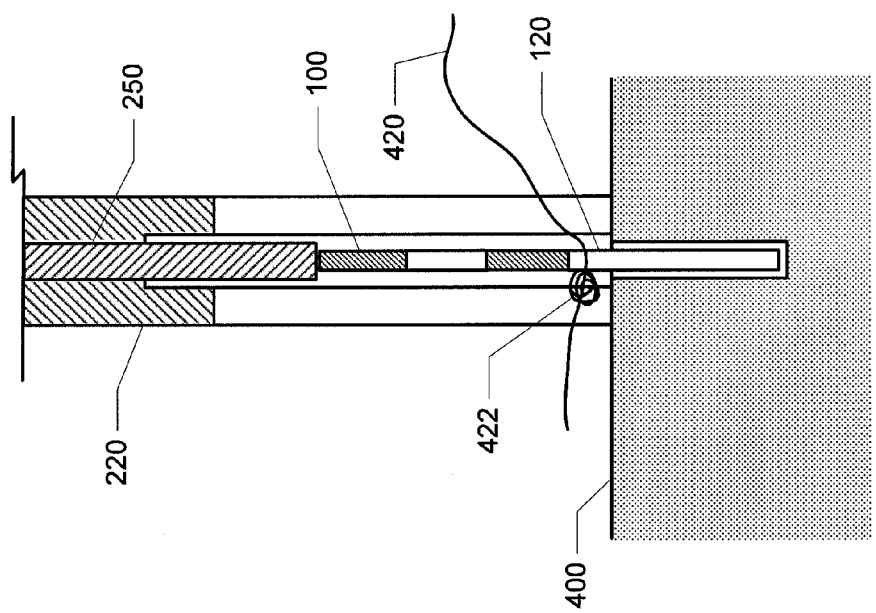
FIG. 6 is a view of an example according to embodiments disclosed herein.

Referring now to FIG. 6, an example of another alternative technique of engaging the suture 420 is shown. In this example, a surgeon has tied a knot 422 in the suture 420 of such size that the knot 422 is too large to pass through the suture-engaging slot 120 of the suture anchor 100. Further, the surgeon has tied the knot 422 on the opposite side of the suture anchor 100 from the side where any tension may be applied to the suture 420. Accordingly, once the suture anchor 100 is driven into the bone 400 by the driver rod 250, the knot 422 will prevent the suture 420 from being pulled through the suture-engaging slot 120, thereby anchoring the suture 420 to the bone 400.

A method of inserting a suture anchor, in accordance with embodiments disclosed herein, may include providing a suture anchor having two substantially flat surfaces and a bifurcated tip, mechanically engaging a suture with the suture anchor, and inserting the suture anchor into a bone. The bifurcated tip may include two sharpened points for insertion into the bone. In one or more embodiments, mechanically engaging the suture with the suture anchor may involve passing the suture through a transverse opening between the two substantially flat surfaces of the suture anchor, or passing the suture through a suture-engaging slot defined by the bifurcated tip. Further, in one or more embodiments, mechanically engaging the suture with the suture anchor may also involve tying a knot in the suture, where the knot is too large to pass through the suture-engaging slot defined by the bifurcated tip. Furthermore, in one or more embodiments, inserting the suture anchor into the bone may involve providing an impact force on a driver rod in mechanical engagement with the suture anchor.

A method of anchoring a suture, in accordance with embodiments disclosed herein, may include passing a first portion of the suture through a transverse opening of a first suture anchor, inserting the first suture anchor into a bone at a first location to fix the first portion of the suture at the first location, passing a second portion of the suture in a bifurcated tip of a second suture anchor, and inserting the second suture anchor into the bone at a second location to fix the second portion of the suture at the second location. The first and second suture anchors may be substantially identical. The transverse opening may be between two substantially flat parallel surfaces of the first suture anchor. Further, in one or more embodiments, the bifurcated tip may include two sharpened points for insertion into the bone. Furthermore, in one or more embodiments, inserting the first suture anchor and inserting the second suture anchor may be performed using an installation tool having an outer tube, a driver rod disposed within the outer tube, a recessed cavity disposed on a distal end of the outer tube, and an impact surface engaged to the driver rod.

Advantageously, embodiments disclosed herein may provide a suture anchor that may be inserted into a bone without requiring a predrilled borehole to receive the suture anchor. In particular, the suture anchor may have a substantially flat body and a bifurcated tip configured to enable insertion into the bone without requiring a borehole, and without causing excess damage to the bone. Further, the suture anchor may include a transverse opening to enable the suture anchor to be tied to a suture, as well as a suture-engaging slot to capture a suture.

Embodiments disclosed herein may also provide an installation tool to install the suture anchor into the bone. The installation tool may include a transverse opening to enable a suture to be engaged to the suture anchor prior to insertion into the bone. Further, the installation tool may include a recessed slot to hold the suture anchor until insertion into the bone. Furthermore, the installation tool may also include an impact surface to receive an impact force to drive the suture anchor into the bone.

While embodiments have been described with respect to a limited number of embodiments, those skilled in the art, having benefit of this disclosure, will appreciate that other embodiments can be devised which do not depart from the scope of embodiments disclosed herein. Accordingly, the scope of embodiments disclosed herein should be limited only by the attached claims.

What is claimed is:
1. A suture anchor, comprising:
a distal end having a bifurcated tip;
wherein the bifurcated tip defines a suture-engaging slot;
a proximal end including a driving surface configured to receive an insertion force along a longitudinal axis from a driver rod of an insertion tool;
wherein the longitudinal axis extends between the distal end and the proximal end;
two substantially flat surfaces extending between the distal end and the proximal end,
wherein the two substantially flat surfaces are substantially parallel,
wherein the two substantially flat surfaces are separated by a thickness of no more than about 0.1 inches,
wherein the two substantially flat surfaces extend along an axis perpendicular to the longitudinal axis by a width of no more than about 0.4 inches;
a transverse opening between the two substantially flat surfaces, the transverse opening configured for holding at least one suture;
two exterior edges extending along the longitudinal axis and defined by the thickness; and a plurality of retention barbs disposed along at least a portion of the two exterior edges located proximally of the transverse opening.

2. The suture anchor of claim 1, wherein the ratio of the thickness to the width is selected from within a range of 1:2 to 1:4.

3. The suture anchor of claim 1, wherein the ratio of the thickness to the width is selected from within a range of 1:4 to 1:8.

4. The suture anchor of claim 1, wherein the bifurcated tip comprises two sharpened points for insertion into a bone.

5. The suture anchor of claim 1, wherein the suture anchor is composed of at least a metal, a plastic, or a combination of a metal and a plastic.

6. The suture anchor of claim 1, wherein the suture anchor is composed of a metal selected from a group consisting of stainless steel and titanium.

7. The suture anchor of claim 1, wherein the suture anchor is composed of a plastic selected from a group consisting of PEEK, polyethylene, and PLLA.

8. The suture anchor of claim 1, wherein the suture anchor is composed of PEEK.

9. A system, comprising:
   an insertion tool comprising:
      a proximal end and a distal end;
      a longitudinal axis between the distal end and the proximal end;
      a handle disposed on the proximal end,
      an outer tube extending from the handle along the longitudinal axis and comprising an inner bore;
      a driver rod movably disposed within the inner bore; and
      a recessed cavity disposed on the distal end of the outer tube and aligned with the longitudinal axis,
      wherein the recessed cavity is configured to retain a suture anchor, comprising two substantially flat parallel surfaces, for insertion into a bone; and
   a suture anchor, engaged in the recessed cavity in a first position, and comprising:
      a bifurcated tip defining a suture-engaging slot, the bifurcated tip being disposed within a distal portion of the recessed cavity;
      two substantially flat parallel surfaces
      wherein the two substantially flat surfaces are separated by a thickness of no more than about 0.1 inches,
      wherein the two substantially flat surfaces extend along an axis perpendicular to the longitudinal axis by a width of no more than about 0.4 inches;
      a transverse opening between the two substantially flat surfaces, the transverse opening configured for holding at least one suture;
      two exterior edges extending along the longitudinal axis and defined by the thickness, and;
      a plurality of retention barbs disposed along at least a portion of the two exterior edges located proximally of the transverse opening; and a proximal end including a driving surface configured to receive an insertion force along the longitudinal axis from the driver rod of the insertion tool.

10. The system of claim 9, wherein the insertion tool further comprises a transverse slot disposed on the distal end of the outer tube and extending through the outer tube.

11. The system of claim 9, wherein the driver rod is configured to transfer a mechanical force to the suture anchor along the longitudinal axis to insert the suture anchor into a bone.

* * * * *